US00PP24800P2

(12) United States Plant Patent
de Bont

(10) Patent No.: US PP24,800 P2
(45) Date of Patent: Aug. 19, 2014

(54) ***ECHINACEA* PLANT NAMED 'GREENLINE'**

(50) Latin Name: ***Echinacea* hybrid**
Varietal Denomination: Greenline

(71) Applicant: Dionysius F. M. de Bont, Gouda (NL)

(72) Inventor: Dionysius F. M. de Bont, Gouda (NL)

( * ) Notice: Subject to any disclaimer, the term of this patent is extended or adjusted under 35 U.S.C. 154(b) by 0 days.

(21) Appl. No.: 13/986,123

(22) Filed: Apr. 3, 2013

(51) Int. Cl.
*A01H 5/00* (2006.01)

(52) U.S. Cl.
USPC ..... Plt./428

(58) Field of Classification Search
USPC ..... Plt./428
See application file for complete search history.

*Primary Examiner* — June Hwu
*Assistant Examiner* — Keith Robinson
(74) *Attorney, Agent, or Firm* — Penny J. Aguirre

(57) ABSTRACT

A new cultivar of hybrid *Echinacea*, 'Greenline', that is characterized by its anemone-type inflorescences, its ray florets that are yellow-green when opening and mature to green-white with a yellow-green tip, its petaloid disk florets that are green-white when opening and mature to green-white with a yellow-green tip, and its strong stems.

2 Drawing Sheets

Botanical classification: *Echinacea* hybrid.
Variety denomination: 'Greenline'.

BACKGROUND OF THE INVENTION

The present invention relates to a new and distinct cultivar of *Echinacea* of hybrid origin and will be referred to hereafter by its cultivar name, 'Greenline'. 'Greenline' represents a new coneflower, an herbaceous perennial grown for landscape use.

The Inventor selected the new cultivar, 'Greenline', in a seedbed at a nursery in Sint Annaland, The Netherlands in August of 2008. The seedbed had been planted with seeds collected and pooled from unnamed proprietary plants of *Echinacea purpurea* and unnamed proprietary plants of hybrid *Echinacea*. The exact parents are therefore unknown.

Asexual propagation of the new cultivar was first accomplished by in vitro propagation under the direction of the Inventor in Rijswijk, Zuid Holland, The Netherlands in September of 2010. Asexual propagation by in vitro propagation has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Greenline' as a unique cultivar of *Echinacea*.

1. 'Greenline' exhibits anemone-type inflorescences.
2. 'Greenline' exhibits ray florets that are yellow-green when opening and mature to green-white with a yellow-green tip.
3. 'Greenline' exhibits petaloid disk florets that are green-white when opening and mature to green-white with a yellow-green tip.
4. 'Greenline' exhibits strong stems.

The new cultivar can be most closely compared to the cultivars 'Milkshake' (U.S. Plant Pat. No. 20,594) and 'Vanilla Cupcake'. Both are similar to 'Greenline' in having anemone-type inflorescences that are white to white-green in color. 'Milkshake' differs from 'Greenline' in having a taller plant size, and in having inflorescences that are whiter in color. 'Vanilla Cupcake' differs from 'Greenline' in having inflorescences that are whiter in color.

BRIEF DESCRIPTION OF THE DRAWINGS

The plants in the accompanying photographs depict the characteristics of a six month-old plant of 'Greenline' as field grown in Sint Annaland, The Netherlands and placed in a one-gallon container for the photographs.

The photograph in FIG. 1 provides a side view of a plant in bloom.

Figure 1:
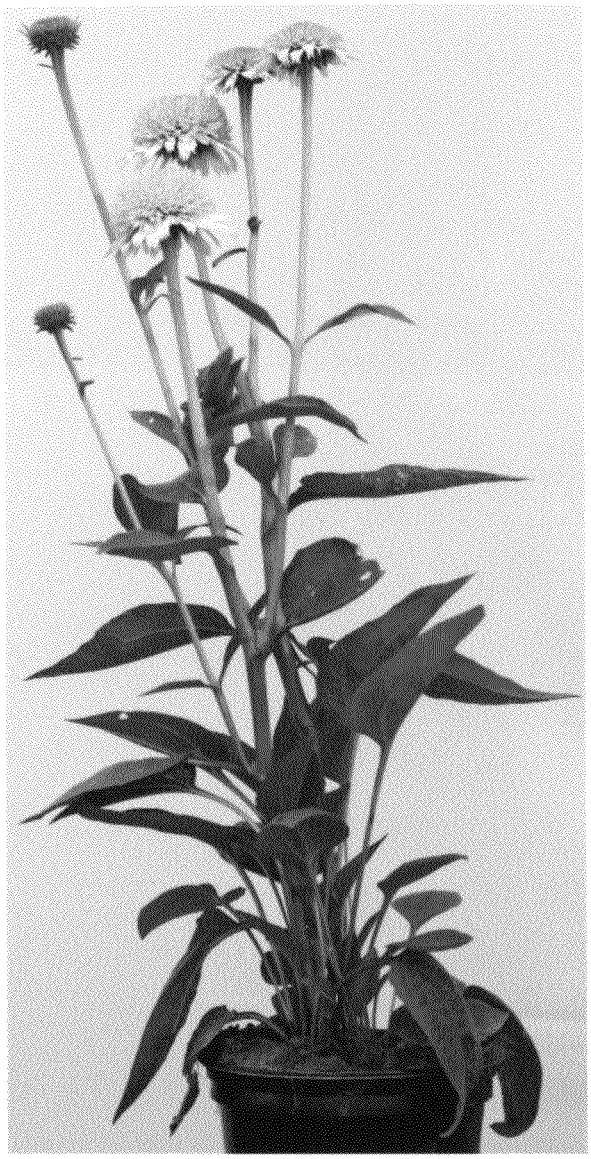
Figure 2:
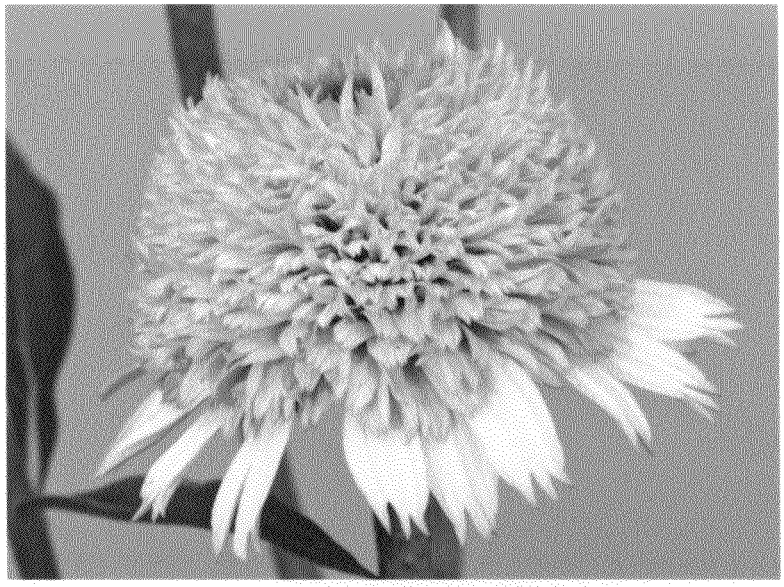

The photograph in FIG. 2 provides a close-up view of an inflorescence of 'Greenline'.

Figure 3:
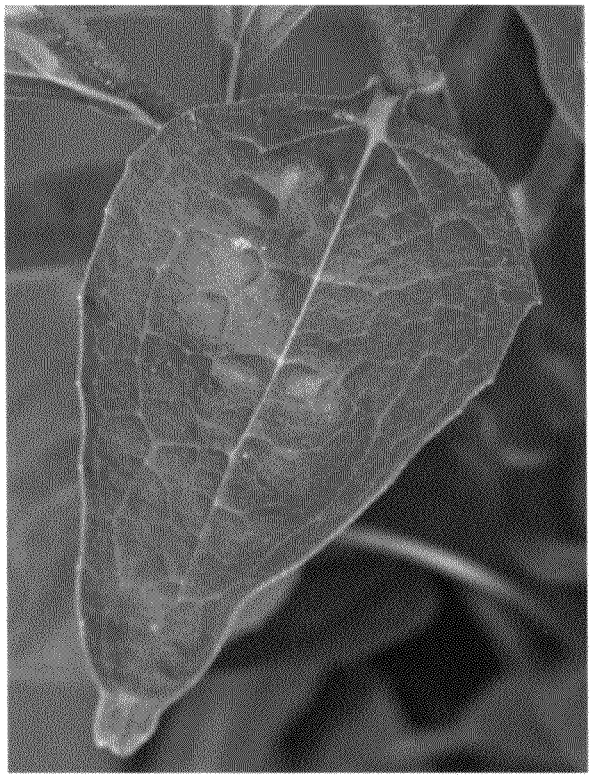

The photograph in FIG. 3 provides a close-up view of a leaf of 'Greenline'.

The colors in the photograph may differ slightly from the color values cited in the detailed botanical description, which accurately describe the colors of the new *Echinacea*.

BOTANICAL DESCRIPTION OF THE PLANT

The following is a detailed description of six month-old plants of the new cultivar as field grown in Sint Annaland, The Netherlands. Plants were grown under average day temperatures ranging from 15° to 32° C. and average night temperatures of 12° to 20° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—July into September in The Netherlands.

*Plant type.*—Herbaceous perennial.

*Plant habit.*—Clump forming, upright with strong stems.

*Height and spread.*—About 65 cm in height and 35 cm in spread.

*Cold hardiness.*—At least to U.S.D.A. Zones 3 to 4.

*Diseases and pests.*—Not more susceptible to pests or diseases than other *Echinacea* varieties.

*Root description.*—Fibrous.

*Propagation.*—Tissue culture.

*Growth rate.*—Moderately vigorous.

Stem description:

*Shape.*—Rounded.

*Stem color.*—144A.

*Stem size.*—Main stem; an average of 9 mm in diameter and 36.2 cm in length.

*Stem surface.*—Slightly rough to the touch due to being densely covered with very short strigose hairs; 0.5 mm in length and NN155D in color.

*Stem strength.*—Strong.

*Branching.*—Un-branched.

Foliage description:

*Leaf shape.*—Ovate to narrowly ovate.

*Leaf division.*—Simple.

*Leaf base.*—Short attenuate.

*Leaf apex.*—Acute.

*Leaf venation.*—Pinnate, upper and lower surface color; 145A to 145B.

*Leaf margins.*—Entire to coarsely and shallowly dentate.

*Leaf attachment.*—Petiolate.

*Leaf arrangement.*—Alternate.

*Internode length.*—An average of 5.5 cm.

*Leaf size.*—Average of 11 cm in length and 6.8 cm in width.

*Leaf color.*—Young upper surface; 137A to 137B, young lower surface; 137C, mature upper surface; N137B, mature lower surface; 137C.

*Leaf surface.*—Upper and lower surface is slightly glossy and densely covered with very short strigose hairs; average length of 0.3 mm and NN155D in color.

*Petioles.*—Upper stem leaves nearly sessile, average length of stem leaves is 2.4 cm in length, v-shaped petiole is about 3 mm in length and width, color; upper side 144C, margins 137A, lower side 144A, margins 143A, upper side smooth, lower side margins and vein moderately covered with very short strigose hairs, average of 0.3 mm in length and NN155D in color.

Flower description:

*Type.*—Terminal capitulum, anemone-type.

*Capitulum number.*—An average of 3 capitulums per stem.

*Lastingness of inflorescence.*—About 10 days.

*Capitulum size.*—Matures to about 5.2 cm in height and 7.1 cm in diameter, disk size is an average of 5.6 cm in diameter.

*Fragrance.*—Faint and sweet.

*Involucral bracts or phyllary.*—About 60 arranged in 3 overlapping rows, up to 0.8 cm in length and 3 mm in width, dull in appearance, cuneate at base, acuminate apex, ovate in shape, entire margins sparsely covered with very short hairs; 0.5 mm in length and 157D in color, upper surface; smooth and N144A, base 145D in color, lower surface; 143B, margins 143A and 141B in color.

*Buds.*—Flattened globular in shape, immature ray florets near vertical, 4.4 cm in diameter and 2.2 cm in length, color; 144A, immature ray florets 145B.

*Peduncle.*—Strong, straight on top of main (flowering) stem, average angle of secondary and tertiary peduncles 30° (0°=straight upright), terminal peduncle length is 12.5 and 5 mm in diameter, 144C, becoming 144A near the inflorescence, surface is densely covered with short strigose hairs; 0.5 mm in length and NN155D in color.

*Ray florets.*—Rotate, about 21, oblanceolate in shape, about 3.3 cm in length and 0.9 cm in width, praemorse apex, cuneate base, entire margin, slightly drooping in an average angle of 30° downward, upper surface is smooth moderately velvety and moderately ribbed lengthways (carinate), lower surface texture is smooth and moderately ribbed lengthways (carinate), color: when opening upper surface; 145D, when opening lower surface; 145C, when fully open upper surface; 157A, tip 145D, when fully open lower surface; 145C, tip 145B.

*Disk florets* (*bisexual*).—Typical disc florets are not present, but are transformed into two ray floret-like petals, one is broad and one is narrow; broad petal: oblanceolate in shape, praemorse apex, cuneate base, entire margin, 2.1 cm in length, 0.6 cm in width, upper side is smooth, dull and velvety, lower side is smooth, dull and slightly glossy, narrow petal; linear in shape, bluntly acute apex, cuneate base, entire margin, 2 cm in length and 0.2 cm in width, upper side is smooth, dull and velvety, lower side is smooth, dull and slightly glossy, color of both ray floret petals; when opening upper side is 157A, tip is 145B, when opening lower side is 145C, tip is 145A, when fully open lower side is 157D, tip is 157A, when fully open lower surface is 145D, tip is 145B; disc size 4 cm in height and 6 cm in diameter.

*Receptacle.*—Cone shaped, about 1.7 cm in diameter and 1.8 cm in height, color is 155B.

*Receptacle spines.*—Average of 340, acicular in shape, acute apex, attenuate base, smooth and glossy surface, color: apex; 17B, mid-section; 144A, base; 144D; 8 mm in length.

Reproductive organs:

*Location of pistils and stamens.*—Disk florets only.

*Gynoecium.*—Pistil; 1, 5 mm in length, style; 4 mm in length and 145C in color, ovary; 145D in color.

*Androcoecium.*—Stamens; 4, filament 3 mm in length and 199D in color, anther; linear in shape, 2 mm in length and N199B in color, no pollen detected.

*Fruit/seed.*—No fruit or seed detected to date.

It is claimed:

1. A new and distinct cultivar of *Echinacea* plant named 'Greenline' substantially as herein illustrated and described.

* * * * *